United States Patent [19]

Shockey et al.

[11] Patent Number: 4,947,864
[45] Date of Patent: Aug. 14, 1990

[54] GUIDEWIRE EXCHANGE CATHETER

[75] Inventors: Rick L. Shockey, Eagan; Mark A. Rydell, Golden Valley, both of Minn.

[73] Assignee: Schneider (U.S.A.), Inc. A Pfizer Company, Minneapolis, Minn.

[21] Appl. No.: 482,907

[22] Filed: Feb. 22, 1990

Related U.S. Application Data

[62] Division of Ser. No. 322,363, Mar. 13, 1989.

[51] Int. Cl.$^5$ .............................................. A61B 5/00
[52] U.S. Cl. ..................................... 128/772; 128/657; 604/53; 604/164; 604/280
[58] Field of Search ..................... 128/343, 344, 348.1, 128/656–658, 637, 772; 604/43, 53, 96, 101, 102, 160, 164, 280, 281, 283

[56] References Cited

U.S. PATENT DOCUMENTS 3,528,406  9/1790  Jeckel et al. ........................ 128/772

4,704,111  11/1987  Moss ................................... 604/280

Primary Examiner—Randall L. Green
Assistant Examiner—Randy Shay
Attorney, Agent, or Firm—Haugen and Nikolai

[57] ABSTRACT

A catheter for facilitating the exchange of guidewires during the course of a transluminal angioplasty or related procedure which comprises an elongated, flexible, tubular member having at least one lumen running the full length thereof from its proximal end to its distal end and which at least three apertures or ports extending through the wall thereof at longitudinally spaced locations near the distal end of the tubular member. These ports communicate with the lumen of the tubular member and a longitudinal slit is also provided through the wall of the tubular member connecting the most proximal port to the next proximal port. The exchange catheter may also include a proximal hub connected to the proximal end of the elongated plastic tube.

1 Claim, 2 Drawing Sheets

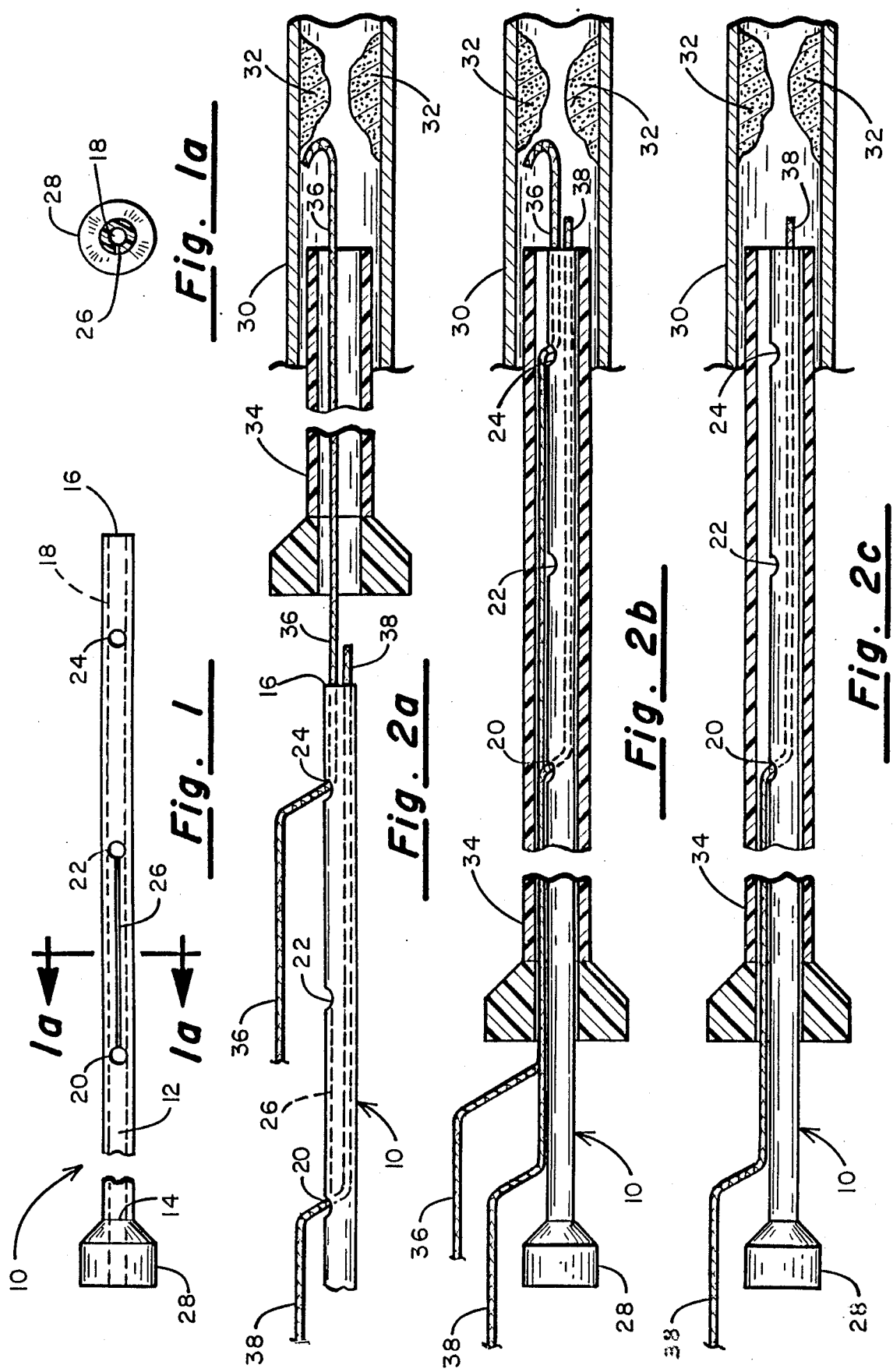

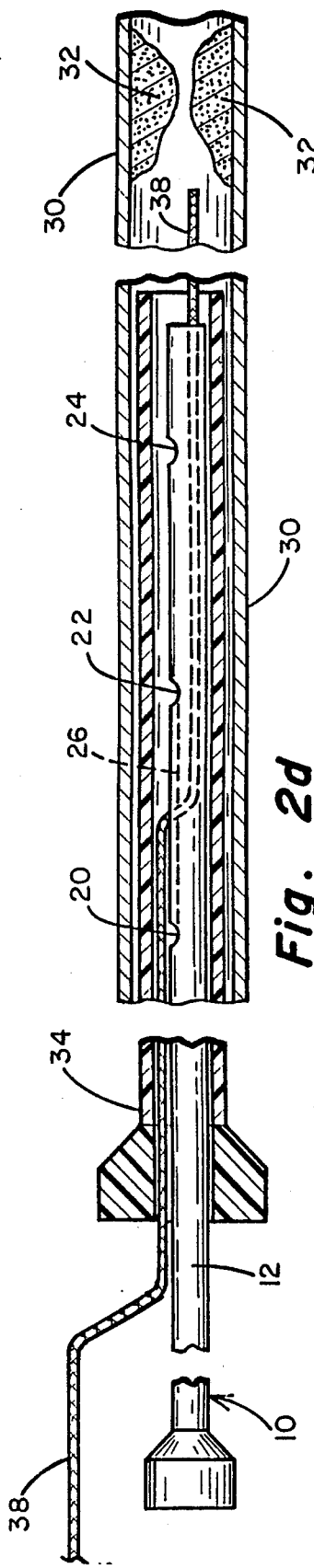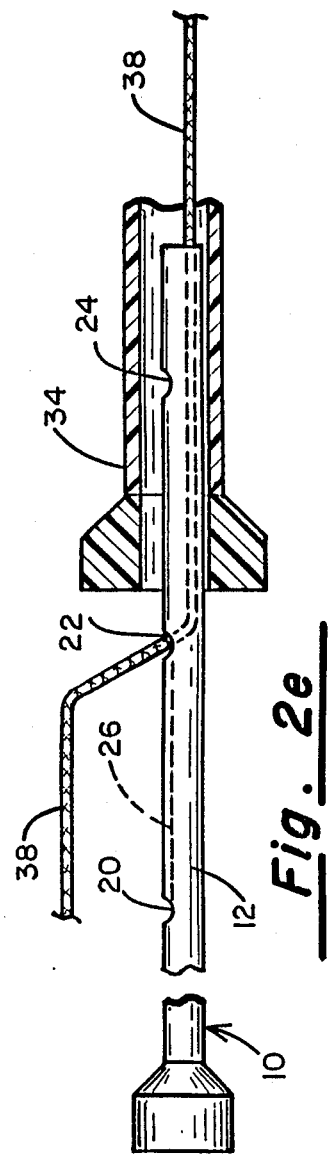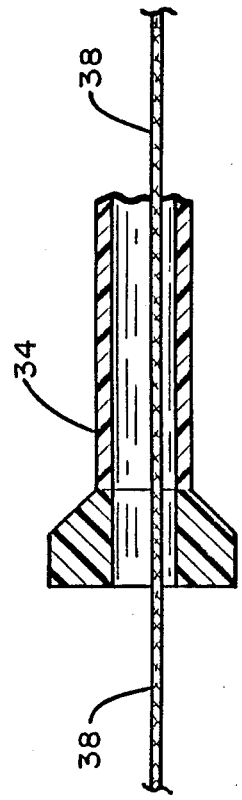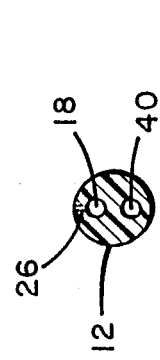

GUIDEWIRE EXCHANGE CATHETER

This is a divisional of application Ser. No. 322,363 filed Mar. 13, 1989.

BACKGROUND OF THE INVENTION

I. Field of the Invention: This invention relates generally to catheter apparatus for carrying out a variety of medical procedures and more particularly to an exchange catheter for facilitating the exchange of one catheter guidewire for another when required for effectively carrying out the catheterization procedure.

II. Discussion of the Prior Art: Since its introduction in the mid-1970's by Dr. Andreas Gruentzig, coronary transluminal angioplasty, using a balloon catheter, has become a recognized method for treating obstructed coronary blood vessels. In carrying out this procedure, an incision may typically be made in the patient's thigh to gain access to the femoral artery and an introducer is inserted into the wound. Next, a guiding catheter is passed through the introducer and routed through the vascular system until the distal end of the guiding catheter reaches the coronary ostium. Following that, a flexible guidewire is inserted through the guiding catheter until its distal end exits the distal end of the guiding catheter. The surgeon, by manipulating the proximal end of the guidewire, attempts to pass it across the stenotic lesion which is obstructing the coronary artery to be treated. Once the guidewire has been made to cross the lesion, a balloon angioplasty catheter is passed over the guidewire by inserting the proximal end of the guidewire into the distal end of the balloon catheter and then pushing the balloon catheter over the guidewire until the balloon on the distal end of the balloon catheter is adjacent the lesion to be treated. Once so positioned, the balloon is inflated to thereby press the stenotic lesion against the wall of the blood vessel and restoring patency to the treated blood vessel.

The above-described procedure assumes the use of a so-called over-the-wire balloon angioplasty catheter. A more recent innovation is the so-called Monorail TM catheter in which only a small distal segment of the balloon catheter actually passes over the guidewire with the remaining portion of the guidewire then extending generally along the exterior wall of the balloon catheter in the proximal direction. The Monorail TM catheter and its use is more particularly described in the Bonzel U.S. Pat. 4,762,129.

It frequently occurs during the conduct of a balloon angioplasty procedure that an originally selected guidewire may turn out not to be suitable for easily passing the stenotic lesion. It thus often becomes necessary to substitute an alternate guidewire. For example, to arrive at the site of the lesion, it may be necessary to employ a guidewire having a particular shape configuration on its distal end. However, with the guidewire so shaped, it may not easily traverse the lesion once the site is arrived at. Thus, the first catheter guidewire must be withdrawn and replaced with a second whose tip may more readily traverse the lesion.

The present invention is directed to a special purpose catheter for facilitating the exchange of guidewires used in angiography and/or angioplasty procedures using the Monorail TM catheter system. The exchange catheter is so designed that it can be used to transport the distal end portion of a new guidewire to the location within the vascular system reached by the distal end of the first guidewire by using the first guidewire as the rail along which the exchange catheter is routed. Once this maneuver has been accomplished, the first guidewire may be stripped out of the exchange catheter and the guide catheter containing it. Then, the exchange catheter itself can be withdrawn from the guide catheter without disturbing the replacement guidewire.

It is accordingly a principal object of the present invention to provide a new surgical tool for facilitating the conduct of transluminal angioplasty and/or angiography procedures.

Another object of the invention is to provide a surgical implement for facilitating the exchange of guidewires used during angiographic and angioplasty procedures.

Still another object of the invention is to provide an exchange catheter for use in a Monorail TM system for allowing a first selected guidewire to be replaced with a second guidewire without losing the positional advantage gained during the installation of the first guidewire. That is to say, using the apparatus and procedure of the present invention, it is no longer necessary to strip out the first guidewire from the guide catheter before the new guidewire is installed to the point where its distal end is at the location occupied by the distal end of the first guidewire before it is withdrawn.

SUMMARY OF THE INVENTION

The foregoing objects and advantages of the present invention are achieved by providing an exchange catheter having elongated flexible plastic tubular member whose outside dimensions permit it to be readily inserted through the lumen of a guide catheter. Located just proximal of the distal end of the tubular member are three longitudinally spaced parts which extend through the wall of the tubular member so as to communicate with the central lumen. A longitudinal slit is also formed through the wall of the tubular member extending from the most proximal port to the second most proximal port.

When, during the course of a surgical catheterization procedure, it is desired to replace an existing guidewire whose tip had been advanced to a predetermined site beyond the distal end of a guide catheter, the distal end of the replacement or second guidewire is fed through the most distal port of the exchange catheter and advanced through the exchange catheter until its distal end is at the distal end of the exchange catheter. Next, the proximal end of the first guidewire is threaded into the distal end of the exchange catheter and out from the most distal port. While gripping the original or first guidewire near its proximal end, the physician advances the exchange catheter into the proximal end of the guide catheter and along the first guidewire until the distal end of the exchange catheter reaches the distal end of the first guidewire. As the exchange catheter is so advanced through the guide catheter, it carries the replacement or second guidewire along with it. The surgeon may now hold the proximal end of the exchange catheter against longitudinal movement as he strips the original guidewire out of the guide catheter. At this point, the distal end of the exchange catheter and the distal end of the replacement or second guidewire remain at the former location of the distal end of the first guidewire.

Now, by holding the second guidewire at its proximal end to prevent longitudinal movement thereof, the surgeon may now strip back the exchange catheter which will ride along the replacement guidewire, the guidewire fitting through the longitudinal slit provided between the most distal and second-most distal ports in the exchange catheter.

When the exchange catheter has been withdrawn from the guide catheter to the point where the second-most distal or middle port becomes visible with the second guidewire extending out of it, the surgeon may readily strip the remaining few inches of the exchange catheter off from the proximal end of the guidewire leaving only the guidewire in position within the lumen of the guide catheter. This completes the exchange procedure and the surgeon may continue on with the remainder of the particular catheterization procedure which is underway.

DESCRIPTION OF THE DRAWINGS

The foregoing features, objects and advantages of the invention will become more apparent to those skilled in the art from the following detailed description of a preferred embodiment, especially when considered in conjunction with the accompanying drawings in which like numerals in the several views refer to correspondingly parts.

FIG. 1 is a side elevational view of the exchange catheter of the present invention;

FIG. 1A is a cross-sectional view taken along line 1a-1a in FIG. 1.

FIGS. 2A through 2F are a series of side elevational views, partially in cross-section, helpful in understanding the way in which the exchange catheter of FIG. 1 is used; and FIG. 3 is a cross-sectional view of an alternative, bi-lumen exchange catheter taken at the same location as the cross-sectional view of FIG. 1A.

DESCRIPTION OF THE PREFERRED EMBODIMENT

Referring to FIGS. 1 and 1A, there is indicated generally by numeral 10 the exchange catheter of the present invention. It is seen to include an elongated, flexible, plastic, tubular member 12 having a proximal end 14 and a distal end 16 and with at least one internal lumen 18 (FIG. 1A) extending the entire length thereof. A further lumen (not shown) may be provided for allowing distal dye injection for visualizing the treatment site. The tubular member 12 is preferably formed from any one of a number of medical grade plastics commonly used in the fabrication of intravascular catheters and including, for example, polyurethane, polyethylene, tetrafluoroethylene fluorocarbon polymer and nylon. Without limitation, the exchange catheter may typically have an outside diameter of about 1.2 mm and an internal diameter of 0.8 mm. As will become more apparent as the description of the preferred embodiment progresses, the outside diameter of the exchange catheter 10 must be sufficiently small so as to be able to readily pass through the lumen of a guide catheter. The internal diameter of the lumen 18 of the exchange catheter must be sufficiently large to permit two guidewires to pass there along.

With continued reference to FIG. 1, it can be seen that toward the distal end 16 of the exchange catheter, there is provided a series of three longitudinally spaced ports, the most proximal being identified by numeral 20, the next most proximal by numeral 22 and the most distal by numeral 24. These ports pass entirely through the side wall of the tubular member 12 so as to communicate with the lumen 18. As is shown in the cross-sectional view of FIG. 1A, a longitudinal slit 26 extends through the thickness of the wall between the most proximal port 20 and the second-most proximal port 22.

Affixed to the proximal end 14 of the tubular member 12 is a molded plastic hub 28 of a conventional design.

Having described the physical construction of the exchange catheter of the present invention, there will next be provided a detailed explanation of the manner in which it is used to effect a substitution of a second guidewire for a first during the course of a diagnostic or angioplasty procedure. In this regard, reference will be made to the series of views labeled FIGS. 2A through 2F.

Referring first to FIG. 2A, numeral 30 is used to identify the walls of a blood vessel, such as a coronary artery, which is partially plugged by a stenotic lesion 32 to be treated. Using the Seldinger technique, an incision is made in the patient's leg to gain access to the femoral artery and a guide catheter 34 has been advanced through an introducer (not shown) and routed through the vascular system to the coronary ostium. Following that, a first guidewire, here identified by numeral 36, has been fed through the guide catheter 34, but upon reaching the site of the stenotic lesion 32, it was determined that the type of distal tip configuration on the guidewire 36 would not allow it to pass through the constriction in the blood vessel defined by the stenotic lesion 32. Hence, the surgeon has decided to substitute a second guidewire 38 having a different distal tip configuration thought to be suitable for crossing the stenotic lesion 32.

To avoid the necessity of totally withdrawing the first guidewire 36 and starting over, in accordance with the present invention, the exchange catheter 10 is brought into play in the following manner. As a first step, the distal end portion of the replacement guidewire 38 is threaded through the most proximal port 20 located near but proximal to the distal end of the exchange catheter 10 and advanced until its distal end protrudes slightly beyond the distal end 16 of the exchange catheter. Next, the proximal end of the original guidewire 36 is threaded through the lumen 18 of the exchange catheter at its distal end 16 and made to pass outwardly therefrom through the distal port 24.

The surgeon next pushes the exchange catheter 10 in the distal direction along the original guidewire 38 and through the lumen of the guide catheter 34 while holding on to the proximal end of the guidewire 38 to prevent its movement. When the distal tip 16 of the exchange catheter is close to the distal end of the first guidewire 36 in the coronary artery being treated, as shown in FIG. 2B, the surgeon pulls back on the original guidewire 36 completely removing it from the exchange catheter and guide catheter while leaving the replacement guidewire 38 near or at the site of the lesion. See FIG. 2C.

The next step is to remove the exchange catheter 10 from the new guidewire 38 so as to leave it by itself within the lumen of the guide catheter 34. To do this, the surgeon grips the proximal end of the guidewire 38 while pulling back on and thereby peeling the exchange catheter 10 from guidewire 38. During this step, and as illustrated in FIG. 2D, the guidewire 38 passes through the slit 18 formed through the wall of the exchange catheter 10 between the ports 20 and 22. This procedure leaves the distal end of the replacement guidewire 38 at or near the site of the lesion 32 which had earlier been approached by the original guidewire 36.

The step of pulling and peeling the exchange catheter 10 relative to the replacement guidewire 38 continues until port 22 in the exchange catheter becomes visible as it exits the proximal hub of the guide catheter 34. When the exchange catheter has been peeled to the point where the guidewire 38 is exiting the exchange catheter 10 at port 22 (FIG. 2E), the surgeon discontinues the peeling action and then proceeds to pull the remaining relatively short distal end portion of the exchange catheter from the proximal end of the guide catheter. The surgeon may then readily strip the remaining portion of the exchange catheter free from the guidewire 38, completing the guidewire exchange procedure as reflected in the view of FIG. 2F.

Using the procedure and exchange catheter of the present invention, a guidewire substitution can be made without the need for an extension wire which had heretofore been required when using over-the-wire catheter technology. The surgeon may readily change one type of guidewire for another, either to alter the maneuverability of the distal end thereof or to provide a different type of distal tip on the guidewire allowing it to pass across a serious blood vessel obstruction. The use of the exchange catheter will maintain the position achieved while using a first guidewire relative to the lesion being treated, but allowing the substitution of a second guidewire for the first. For example, if it is assumed that the first guidewire is in the distal coronary artery but manipulation of that guidewire does not result in steering it down a torturous distal path, instead of pulling the first guidewire and losing position in the artery, the exchange catheter 10 of the present invention is fed down the first guidewire 36, carrying a new type of guidewire. Once the exchange catheter is close to the distal tip of the first guidewire, the first guidewire can be removed, followed by the removal of the exchange catheter itself leaving the replacement guidewire at the desired location.

It has also been found expedient to utilize an exchange catheter having two lumens as is illustrated in the cross-sectional view of FIG. 3. Again, the lumen 18 is used to receive the guidewires 36 and 38 while the additional lumen 40 is available to allow pressure measurements to be taken both proximal and distal to the lesion being treated whereby an accurate pressure gradient can be measured to assess the efficacy of the balloon angioplasty procedure. The lumen 40 may also be used to inject a contrast medium for visualizing the site being treated or, alternatively, to profuse blood or other nutrient to the site of the lesion.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for exchanging a first guidewire used with a guide catheter disposed within the vascular system of a living body for a second guidewire comprising the steps of:

(a) providing an elongated flexible plastic tubular member having a proximal end and a distal end with a first lumen extending the entire length thereof and having at least three spaced-apart apertures longitudinally aligned a relatively short distance from said distal end and extending through the side wall of said tubular member to said first lumen, with a slit extending through said wall to said first lumen between the most proximal and second-most proximal ones of said spaced-apart apertures;

(b) placing the distal end of said second guidewire through said most proximal aperture in said tubular member and advance the distal end of said second guidewire to said distal end of said tubular member;

(c) inserting the proximal end of said first guidewire through the distal end of said tubular member through a portion of said first lumen and out the most distal one of said aperture;

(d) advancing said tubular member in the distal direction down said first guidewire while restraining movement of said first guidewire until said distal end of said tubular member is close to the distal end of said first guidewire in said vascular system;

(e) withdrawing said first guidewire from said guide catheter;

(f) restraining longitudinal movement of said second guidewire while pulling said tubular member proximally such that a portion of said second guidewire passes through said slit and until said second-most proximal aperture is visible beyond the proximal end of said guide catheter; and (g) releasing the proximal end of said second guidewire and removing the remaining distal portion of said tubular member from said guide catheter and from said second guidewire leaving said second guidewire in place within said guide catheter.

* * * * *

UNITED STATES PATENT AND TRADEMARK OFFICE
CERTIFICATE OF CORRECTION

PATENT NO. : 4,947,864

DATED : August 14, 1990

INVENTOR(S) : Rick L. Shockey, et al

It is certified that error appears in the above-identified patent and that said Letters Patent is hereby corrected as shown below:

On the title page [54] change title of invention to read -- METHOD OF GUIDEWIRE EXCHANGE USING GUIDEWIRE EXCHANGE CATHETER --.

Signed and Sealed this

Eleventh Day of February, 1992

Attest:

HARRY F. MANBECK, JR.

*Attesting Officer*          *Commissioner of Patents and Trademarks*